(12) United States Patent
Iwakiri (10) Patent No.: US 11,520,057 B2
(45) Date of Patent: *Dec. 6, 2022

(54) RADIATION IMAGE CAPTURING APPARATUS

(71) Applicant: FUJIFILM Corporation, Tokyo (JP)

(72) Inventor: Naoto Iwakiri, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/029,977

(22) Filed: Sep. 23, 2020

(65) Prior Publication Data

US 2021/0003719 A1    Jan. 7, 2021

Related U.S. Application Data

(63) Continuation of application No. PCT/JP2019/007502, filed on Feb. 27, 2019.

(30) Foreign Application Priority Data

Mar. 26, 2018   (JP) .............................. JP2018-058966

(51) Int. Cl.
    *G01T 1/17* (2006.01)
    *G01T 1/29* (2006.01)
    *G01T 1/20* (2006.01)

(52) U.S. Cl.
    CPC ............ *G01T 1/17* (2013.01); *G01T 1/20188* (2020.05); *G01T 1/2978* (2013.01); *G01T 1/2964* (2013.01)

(58) Field of Classification Search
    CPC ....... G01T 1/17; G01T 1/2978; G01T 1/2964; G01T 1/20188
    See application file for complete search history.

(56) References Cited

U.S. PATENT DOCUMENTS

| | | | |
|---|---|---|---|
| 2003/0031296 A1* | 2/2003 | Hoheisel | ............... G01T 1/2018 378/98.8 |
| 2006/0181839 A1 | 8/2006 | Yamada | |
| (Continued) | | | |

FOREIGN PATENT DOCUMENTS

| | | |
|---|---|---|
| JP | 2003070776 A | 3/2003 |
| JP | 2008122116 A | 5/2008 |
| (Continued) | | |

OTHER PUBLICATIONS

Adachi—WO 2010/070735 A1—Google Patents English obtained Jan. 12, 2022 (Year: 2022).*

(Continued)

*Primary Examiner* — David P Porta
*Assistant Examiner* — Jeremy S Valentiner
(74) *Attorney, Agent, or Firm* — Studebaker & Brackett PC (57) ABSTRACT

A radiation image capturing apparatus includes a sensor substrate including a flexible base material and plural pixels that accumulate charges generated in accordance with radiation, a flexible first cable including one ends electrically connected to a connection region disposed at a predetermined side of the sensor substrate, a first circuit substrate electrically connected to the other end of the first cable and in which a first component used for processing a digital signal in a circuit unit driven in a case of reading out the charges in the plural pixels is mounted, a flexible second cable including one end electrically connected to a connection region disposed at a side different from the predetermined side, and a second circuit substrate electrically connected to the other end of the second cable and in which a second component used for processing an analog signal in the circuit unit is mounted.

17 Claims, 6 Drawing Sheets

(56) References Cited

U.S. PATENT DOCUMENTS

| | | | |
|---|---|---|---|
| 2007/0001967 A1 | 1/2007 | Hung et al. | |
| 2008/0287747 A1* | 11/2008 | Mestrovic | H05K 1/147 600/300 |
| 2009/0096971 A1 | 4/2009 | Hioki et al. | |
| 2010/0078573 A1* | 4/2010 | Nishino | G01T 1/2018 250/394 |
| 2010/0193691 A1 | 8/2010 | Ishii et al. | |
| 2011/0148748 A1 | 6/2011 | Lee | |
| 2013/0265066 A1 | 10/2013 | Hsieh et al. | |
| 2014/0312238 A1* | 10/2014 | Liu | G01T 1/1618 250/363.03 |
| 2016/0070006 A1* | 3/2016 | Konkle | G01T 1/2018 250/366 |
| 2016/0341689 A1* | 11/2016 | Guenschel | G01N 27/4078 |

FOREIGN PATENT DOCUMENTS

| | | |
|---|---|---|
| JP | 2009-133837 A | 6/2009 |
| JP | 2010085266 A | 4/2010 |
| JP | 2011075327 A | 4/2011 |
| JP | 2012133315 A | 7/2012 |
| TW | 200638319 A | 11/2006 |
| TW | 200703184 A | 1/2007 |
| TW | 201123161 A | 7/2011 |
| TW | 201328349 A | 7/2013 |
| TW | 201341813 A | 10/2013 |
| WO | 2010070735 A1 | 6/2010 |
| WO | WO-2010070735 A1 * | 6/2010 ......... H01L 27/1218 |
| WO | 2013/094805 A1 | 6/2013 |

OTHER PUBLICATIONS

International Search Report issued in PCT/JP2019/007502; dated May 14, 2019.

International Preliminary Report on Patentability and Written Opinion issued in PCT/JP2019/007502; dated Sep. 29, 2020.

An Office Action issued by Taiwan Intellectual Property Office dated Sep. 5, 2022, which corresponds to Taiwanese Patent Application No. 108106734 and is related to U.S. Appl. No. 17/029,977; with partial translation.

* cited by examiner

RADIATION IMAGE CAPTURING APPARATUS

CROSS-REFERENCE TO RELATED APPLICATIONS

This application is a continuation application of International Application No. PCT/JP2019/007502, filed on Feb. 27, 2019, which is incorporated herein by reference in its entirety. Further, this application claims priority from Japanese Patent Application No. 2018-058966, filed on Mar. 26, 2018, the disclosure of which is incorporated by reference herein.

BACKGROUND

Technical Field

The present disclosure relates to a radiation image capturing apparatus.

Related Art

In the related art, a radiation image capturing apparatus that performs radiation imaging for the purpose of medical diagnosis has been known. In such a radiation image capturing apparatus, a radiation detector for detecting radiation transmitted through a subject and generating a radiation image is used.

A radiation detector comprising a sensor substrate in which a plurality of pixels accumulating electric charges generated in accordance with radiation are disposed is present. In such a radiation detector, by electrically connecting a circuit unit disposed outside the sensor substrate to the sensor substrate, the electric charges accumulated in each pixel are read out by driving the circuit unit. Connection between the sensor substrate and the circuit unit is performed by electrically connecting a cable such as a flexible cable to a base material of the sensor substrate.

In addition, a radiation detector using a flexible base material in the sensor substrate has been known (for example, refer to WO2010/070735). By using the flexible base material, for example, the weight of the radiation image capturing apparatus (radiation detector) can be reduced, and imaging of the subject may be facilitated.

A method called a lamination method has been known as an example of a method of manufacturing the radiation detector using the flexible base material in the sensor substrate. In the lamination method, a sheet as the flexible base material is bonded to a support such as a glass substrate. Furthermore, the sensor substrate and a conversion layer are formed. Then, the sensor substrate in which the conversion layer is formed is stripped from the support by mechanical stripping.

In the case of stripping the sensor substrate from the support by mechanical stripping, for example, any side of the outer edge of the sensor substrate is set as a starting point of stripping, and the sensor substrate is gradually peeled from the support from the side as the starting point to the opposite side.

The mechanical stripping may be performed in a state where a circuit substrate on which the circuit unit disposed outside is mounted is electrically connected to the sensor substrate through a cable. In the case of performing the mechanical stripping in such a state, the sensor substrate is bent. Thus, the circuit substrate is also bent in accordance with bending of the sensor substrate, and a problem such as damage to the circuit substrate or a component mounted on the circuit substrate may arise.

SUMMARY

The present disclosure provides a radiation image capturing apparatus capable of suppressing an effect exerted on a circuit unit compared to a case where a first component used for processing a digital signal and a second component used for processing an analog signal coexist in a single substrate.

In order to achieve the above object, a first aspect of the present disclosure is a radiation image capturing apparatus comprising a sensor substrate including a flexible base material and a plurality of pixels accumulating electric charges generated in accordance with radiation, a flexible first cable of which one end is electrically connected to a connection region disposed on a predetermined side of the sensor substrate, a first circuit substrate that is electrically connected to the other end of the first cable and in which a first component used for processing a digital signal in a circuit unit driven in a case of reading out the electric charges accumulated in the plurality of pixels is mounted, a flexible second cable of which one end is electrically connected to a connection region disposed on a side different from the predetermined side of the sensor substrate, and a second circuit substrate that is electrically connected to the other end of the second cable and in which a second component used for processing an analog signal in the circuit unit is mounted.

According to a second aspect of the present disclosure, in the first aspect, the first component may include a component of a driving unit that reads out the electric charges from the plurality of pixels.

According to a third aspect of the present disclosure, in the first aspect or the second aspect, the second component may include a component of a signal processing unit into which an electric signal corresponding to the electric charges accumulated in the plurality of pixels is input and that generates and outputs image data corresponding to the input electric signal.

According to a fourth aspect of the present disclosure, in any one of the first aspect to the third aspect, the first circuit substrate may be a flexible substrate.

According to a fifth aspect of the present disclosure, in any one of the first aspect to the fourth aspect, the first cable may be electrically connected to the sensor substrate by thermocompression.

According to a sixth aspect of the present disclosure, in any one of the first aspect to the fifth aspect, the first cable may be electrically connected to the first circuit substrate by thermocompression.

According to a seventh aspect of the present disclosure, in any one of the first aspect to the sixth aspect, the second circuit substrate may be a non-flexible substrate.

According to an eighth aspect of the present disclosure, in any one of the first aspect to the seventh aspect, the second cable may be electrically connected to the sensor substrate by thermocompression.

According to a ninth aspect of the present disclosure, in any one of the first aspect to the eighth aspect, the second cable may be electrically connected to the second circuit substrate through a connector.

According to a tenth aspect of the present disclosure, in any one of the first aspect to the ninth aspect, the predetermined side may be a longest side of the sensor substrate.

According to an eleventh aspect of the present disclosure, in the first aspect, a plurality of the first components may be mounted in the first circuit substrate, and the second components smaller than the first components in number may be further mounted in the first circuit substrate.

According to a twelfth aspect of the present disclosure, in the first aspect, a plurality of the second components may be mounted in the second circuit substrate, and the first components smaller than the second components in number may be further mounted in the second circuit substrate.

According to the first aspect of the present disclosure, the effect exerted on the circuit unit can be suppressed compared to a case where the first component used for processing the digital signal and the second component used for processing the analog signal coexist in a single substrate.

According to the second aspect of the present disclosure, an effect of electrical interference on the component of the driving unit due to bending of the sensor substrate can be suppressed even in a case where the first component includes the component of the driving unit.

According to the third aspect of the present disclosure, the effect of electrical interference on the component of the signal processing unit due to bending of the sensor substrate can be suppressed compared to a case where the component of the signal processing unit is included in other than the second component.

According to the fourth aspect of the present disclosure, the sensor substrate can be easily bent compared to a case where the first circuit substrate is a non-flexible substrate.

According to the fifth aspect of the present disclosure, the sensor substrate can be easily bent compared to a case where the first cable is electrically connected to the sensor substrate through the connector.

According to the sixth aspect of the present disclosure, the sensor substrate can be easily bent compared to a case where the first cable is electrically connected to the first circuit substrate through the connector.

According to the seventh aspect of the present disclosure, electrical interference in the second component can be suppressed compared to a case where the second circuit substrate is a flexible substrate.

According to the eighth aspect of the present disclosure, the sensor substrate can be easily bent compared to a case where the second cable is electrically connected to the second circuit substrate through the connector.

According to the ninth aspect of the present disclosure, reworking of the second cable can be easily performed compared to a case where the second circuit substrate does not comprise the connector.

According to the tenth aspect of the present disclosure, the effect exerted on the circuit unit can be further suppressed compared to a case where the predetermined side is a side other than the longest side of the sensor substrate.

According to the eleventh aspect of the present disclosure, degradation of the characteristics of the radiation image capturing apparatus can be suppressed compared to a case where the second components larger than the first components in number are mounted in the first circuit substrate.

According to the twelfth aspect of the present disclosure, degradation of the characteristics of the radiation image capturing apparatus can be suppressed compared to a case where the first components larger than the second components in number are mounted in the second circuit substrate.

DESCRIPTION OF EMBODIMENTS

Hereinafter, exemplary embodiments of the present disclosure will be described in detail with reference to the drawings. The present exemplary embodiment does not limit the present disclosure.

First Exemplary Embodiment

A radiation image capturing apparatus of the present exemplary embodiment has a function of capturing a radiation image of an imaging target by detecting radiation transmitted through a subject which is the imaging target and outputting image information representing the radiation image of the subject.

Figure 1:
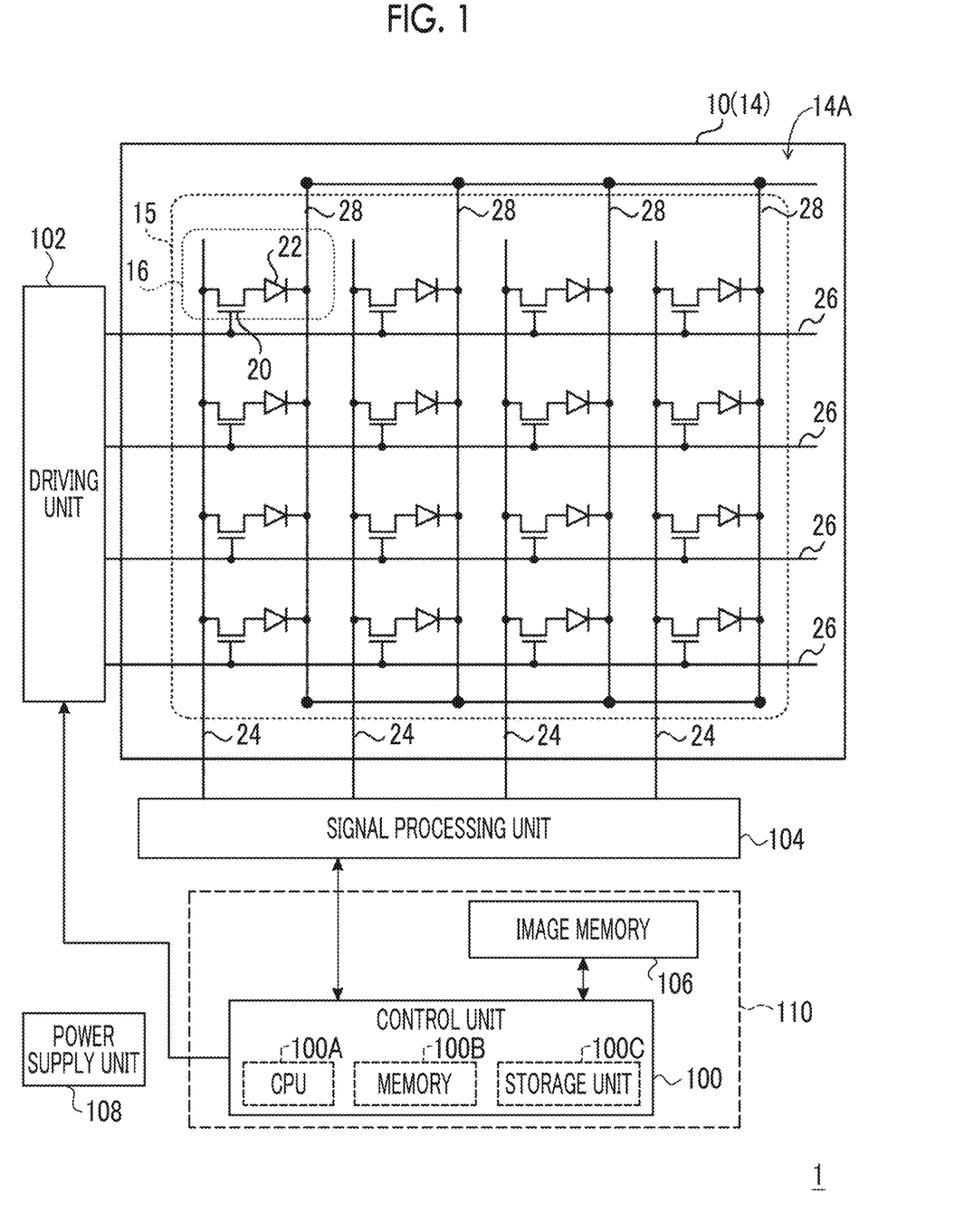
FIG. 1 is a block diagram illustrating one example of a main configuration of an electric system in a radiation image capturing apparatus of a first exemplary embodiment.

First, a summary of one example of a configuration of an electric system in the radiation image capturing apparatus of the present exemplary embodiment will be described with reference to FIG. 1. FIG. 1 is a block diagram illustrating one example of a main configuration of an electric system in a radiation image capturing apparatus of a first exemplary embodiment.

As illustrated in FIG. 1, a radiation image capturing apparatus 1 of the present exemplary embodiment comprises a radiation detector 10, a control unit 100, a driving unit 102, a signal processing unit 104, an image memory 106, and a power supply unit 108.

A radiation detector 10 comprises a sensor substrate 12 (refer to FIG. 2) and a conversion layer (refer to FIG. 2) that converts radiation into light. The sensor substrate 12 comprises a flexible base material 14 and a plurality of pixels 16 disposed on a first surface 14A of the base material 14. Hereinafter, the plurality of pixels 16 may be simply referred to as the "pixels 16".

As illustrated in FIG. 1, each pixel 16 of the present exemplary embodiment comprises a sensor unit 22 that generates electric charges in accordance with the light converted by the conversion layer and accumulates the electric charges, and a switching element 20 that reads out the electric charges accumulated in the sensor unit 22. In the present exemplary embodiment, for example, a thin film transistor (TFT) is used as the switching element 20. Thus, hereinafter, the switching element 20 will be referred to as the "TFT 20". In the present exemplary embodiment, a layer in which the sensor unit 22 and the TFT 20 are formed and furthermore, the pixels 16 are formed is disposed on the first surface 14A of the base material 14 as a flattened layer.

Hereinafter, the layer in which the pixels 16 are formed may be referred to as the "pixels 16" for convenience of description.

The pixels 16 are two-dimensionally arranged in an active area 15 of the sensor substrate 12 in one direction (a scanning wire direction corresponding to a horizontal direction in FIG. 1; hereinafter, referred to as a "row direction") and a direction (a signal wire direction corresponding to a vertical direction in FIG. 1; hereinafter, referred to as a "column direction") intersecting with the row direction. While arrangement of the pixels 16 is illustrated in a simplified manner in FIG. 1, for example, 1024×1024 pixels 16 are arranged in the row direction and the column direction.

In addition, in the radiation detector 10, a plurality of scanning wires 26 that are comprised for each row of the pixels 16 for controlling a switching state (ON and OFF) of the TFT 20 and a plurality of signal wires 24 that are comprised for each column of the pixels 16 and to which the electric charges accumulated in the sensor unit 22 are read out are disposed in intersection with each other. Each of the plurality of scanning wires 26 is electrically connected to a driving unit 102. A control unit 100, described later, is connected to the driving unit 102. The driving unit 102 outputs a driving signal in accordance with a control signal output from the control unit 100. The driving signal output from the driving unit 102 for controlling the switching state by driving the TFT 20 flows through each of the plurality of scanning wires 26. In addition, by electrically connecting each of the plurality of signal wires 24 to a signal processing unit 104, the electric charges read out from each pixel 16 are output to the signal processing unit 104 as an electric signal. The signal processing unit 104 generates and outputs image data corresponding to the input electric signal.

The control unit 100, described later, is connected to the signal processing unit 104, and the image data output from the signal processing unit 104 is sequentially output to the control unit 100. An image memory 106 is connected to the control unit 100, and the image data sequentially output from the signal processing unit 104 is sequentially stored in the image memory 106 under control of the control unit 100. The image memory 106 has a storage capacity in which image data corresponding to a predetermined number of images can be stored. Each time the radiation image is captured, the image data obtained by imaging is sequentially stored in the image memory 106.

The control unit 100 comprises a central processing unit (CPU) 100A, a memory 100B including a read only memory (ROM), a random access memory (RAM), and the like, and a non-volatile storage unit 100C such as a flash memory. One example of the control unit 100 is exemplified by a microcomputer or the like. The control unit 100 controls the operation of the entire radiation image capturing apparatus 1.

In the radiation image capturing apparatus 1 of the present exemplary embodiment, the image memory 106, the control unit 100, and the like are formed in a control substrate 110.

In addition, a common wire 28 is disposed in the sensor unit 22 of each pixel 16 in a wire direction of the signal wire 24 in order to apply a bias voltage to each pixel 16. By electrically connecting the common wire 28 to a bias power supply (not illustrated) outside the sensor substrate 12, the bias voltage is applied to each pixel 16 from the bias power supply.

A power supply unit 108 supplies electric power to various elements and various circuits such as the control unit 100, the driving unit 102, the signal processing unit 104, the image memory 106, and the power supply unit 108. In FIG. 1, wires connecting the power supply unit 108 to various elements and various circuits are not illustrated in order to avoid complication.

Figure 2:
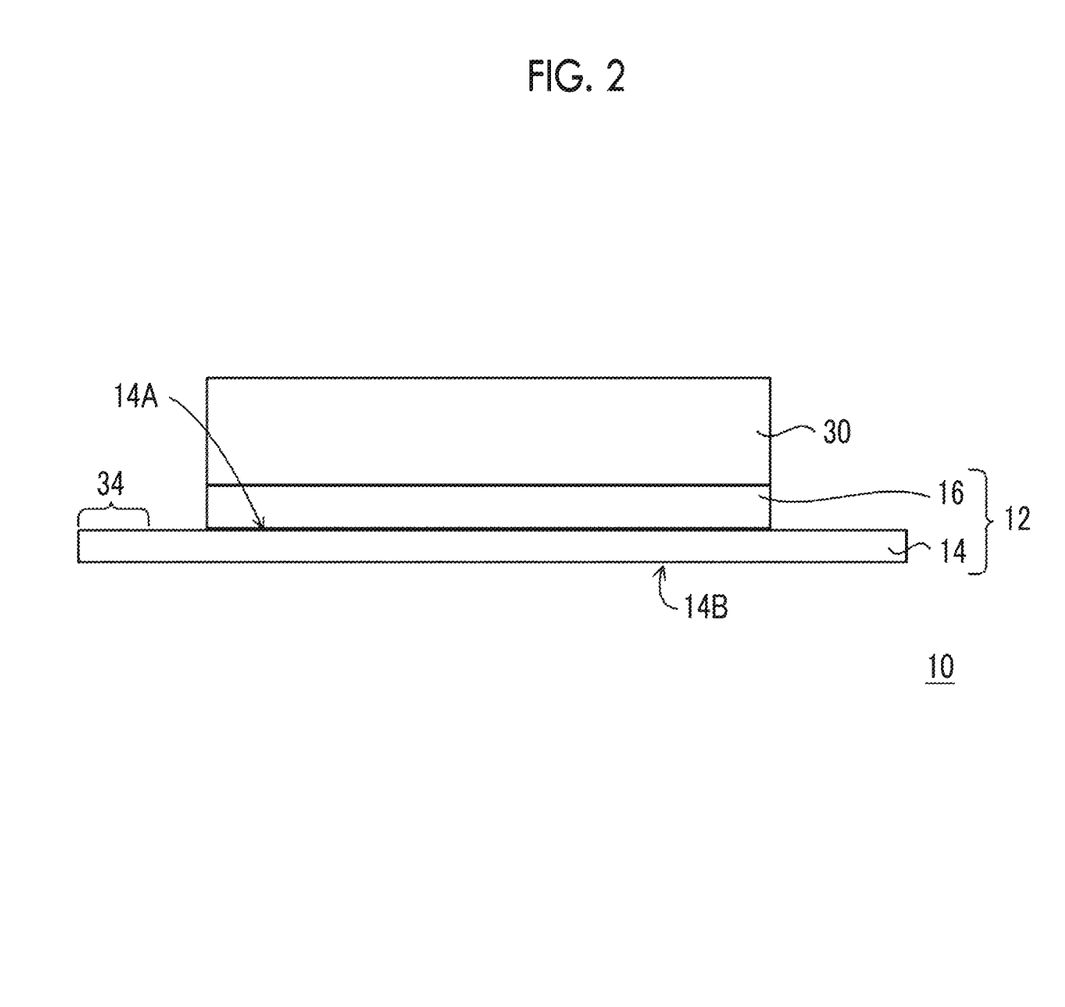
FIG. 2 is a cross-sectional view illustrating a summary of one example of a configuration of a radiation detector of the first exemplary embodiment.

The radiation detector 10 of the present exemplary embodiment will be further described in detail. FIG. 2 is a cross-sectional view illustrating a summary of one example of the radiation detector 10 of the present exemplary embodiment.

As illustrated in FIG. 2, the radiation detector 10 of the present exemplary embodiment comprises the sensor substrate 12 including the base material 14 and the pixels 16, and a conversion layer 30. The base material 14, the pixels 16, and the conversion layer 30 are disposed in this order. Hereinafter, a direction (up-down direction in FIG. 2) in which the base material 14, the pixels 16, and the conversion layer 30 are laminated will be referred to as a lamination direction.

The base material 14 is a resin sheet that has flexibility and includes plastic such as polyimide. A specific example of the base material 14 is exemplified by XENOMAX (registered trademark). The base material 14 is not limited to the resin sheet, provided that the base material 14 has desired flexibility. For example, the base material 14 may be a glass substrate or the like having a relatively small thickness. The thickness of the base material 14 may be a thickness in which desired flexibility is obtained depending on the hardness of the substance, the size (the area of the first surface 14A or a second surface 14B) of the sensor substrate 12, and the like. For example, in a case where the base material 14 is the resin sheet, the thickness may be 5 μm to 125 μm. Alternatively, for example, in a case where the base material 14 is the glass substrate, the base material 14 generally has flexibility in a case where the thickness is less than or equal to 0.1 mm with a size of less than or equal to 43 cm for one side. Thus, the thickness may be less than or equal to 0.1 mm.

As illustrated in FIG. 2, the plurality of pixels 16 are disposed in a partial region inside the first surface 14A of the base material 14. That is, in the sensor substrate 12 of the present exemplary embodiment, the pixels 16 are not disposed in an outer periphery portion of the first surface 14A of the base material 14. In the present exemplary embodiment, a region in which the pixels 16 are disposed on the first surface 14A of the base material 14 is set as the active area 15. In the present exemplary embodiment, for example, the pixels 16 are disposed on the first surface 14A of the base material 14 through an undercoat (not illustrated) using SiN or the like.

In addition, as illustrated in FIG. 2, the outer periphery of the first surface 14A of the base material 14 is set as a terminal region 34 in which a terminal electrically connected to the signal wire 24 or the scanning wire 26 is disposed. The terminal region 34 of the present exemplary embodiment is an example of the connection region of the present disclosure.

In addition, as illustrated in FIG. 2, the conversion layer 30 covers the active area 15. In the present exemplary embodiment, a scintillator including cesium iodide (CsI) is used as one example of the conversion layer 30. For example, it is preferable that such a scintillator includes CsI:Tl (cesium iodide to which thallium is added) or CsI:Na (cesium iodide to which sodium is added) of which the light emission spectrum at the time of X ray irradiation is 400 nm to 700 nm. The light emission peak wavelength of CsI:Tl in a visible light spectrum is 565 nm.

In the present exemplary embodiment, the conversion layer 30 of CsI is directly formed on the sensor substrate 12 as columnar crystal using a vapor deposition method such as a vacuum evaporation method, a sputtering method, and a chemical vapor deposition (CVD) method. In this case, the side of the conversion layer 30 that is in contact with the pixels 16 is set as a base point side of the growth direction of the columnar crystal.

In a case where the conversion layer of CsI is directly formed on the sensor substrate 12 using the vapor deposition method, for example, a reflection layer (not illustrated) having a function of reflecting the light converted by the conversion layer 30 may be disposed on a surface on a side opposite to the side in contact with the sensor substrate 12. The reflection layer may directly disposed in the conversion layer 30 or may be disposed through an adhesive layer or the like. In this case, it is preferable to use an organic-based material as the material of the reflection layer. For example, it is preferable to use at least one of white polyethylene terephthalate (PET), $TiO_2$, $Al_2O_3$, foamed white PET, a polyester-based high reflection sheet, or specular reflection aluminum as the material. Particularly, it is preferable to use white PET as the material from the viewpoint of reflectance.

White PET is obtained by adding a white pigment such as $TiO_2$ or barium sulfate to PET. The polyester-based high reflection sheet is a sheet (film) having a multilayer structure in which a plurality of thin polyester sheets are stacked. Foamed white PET is white PET having a porous surface.

In the case of using the scintillator of CsI as the conversion layer 30, the conversion layer 30 can be formed in the sensor substrate 12 using a different method from the present exemplary embodiment. For example, the conversion layer 30 may be formed in the sensor substrate 12 by preparing an aluminum plate or the like on which CsI is vapor-deposited using the vapor deposition method and bonding the side of CsI not in contact with the aluminum plate to the pixels 16 of the sensor substrate 12 using an adhesive sheet or the like.

Furthermore, unlike the radiation detector 10 of the present exemplary embodiment, $Gd_2O_2S:Tb$ (GOS) or the like may be used as the conversion layer 30 instead of CsI. In this case, for example, the conversion layer 30 can be formed in the sensor substrate 12 by preparing bonding of a sheet obtained by dispersing GOS in a binder of resin or the like to a support formed by white PET or the like using an adhesive layer or the like, and bonding a side of the GOS to which the support is not bonded to the pixels 16 of the sensor substrate 12 using an adhesive sheet or the like.

A protective film or an antistatic film that covers a part or the entirety of the radiation detector 10 or the conversion layer 30 or the like may be disposed. For example, a Parylene (registered trademark) film or an insulating sheet of polyethylene terephthalate or the like is exemplified as the protective film. In addition, for example, a sheet of Alupet (registered trademark) in which an insulating sheet (film) of polyethylene terephthalate or the like is laminated with aluminum by bonding an aluminum foil, or a film using an antistatic paint "Colcoat" (product name; manufactured by Colcoat Co., Ltd.) is exemplified as the antistatic film.

Figure 3:
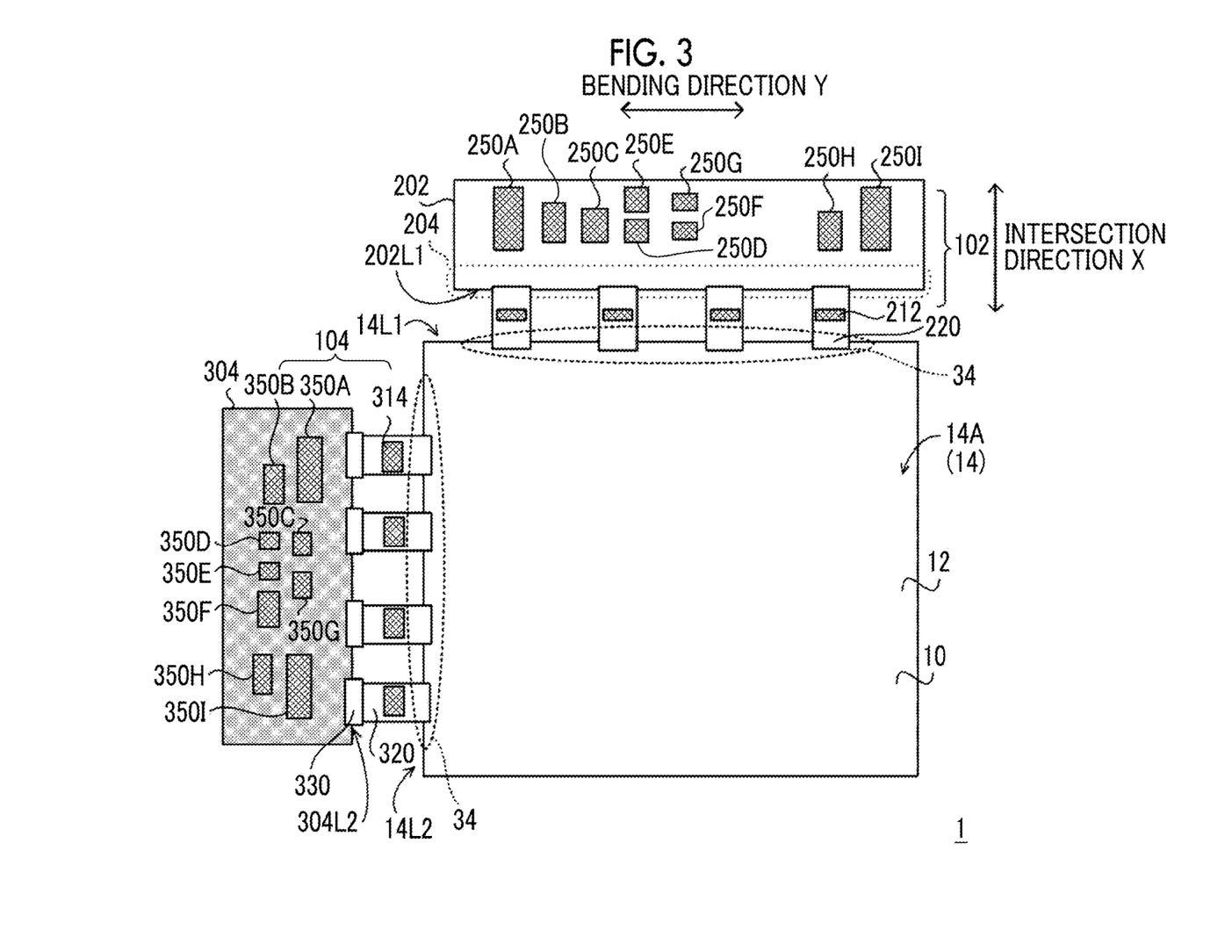
FIG. 3 is a plan view of one example of the radiation image capturing apparatus of the first exemplary embodiment seen from a side of a first surface of a base material.

Next, connection between the radiation detector 10 of the present exemplary embodiment and the driving unit 102 and the signal processing unit 104 will be described in detail. FIG. 3 illustrates a plan view in which one example of a state where the driving unit 102 and the signal processing unit 104 are connected to the radiation detector 10 of the present exemplary embodiment is seen from the first surface 14A side of the base material 14.

As illustrated in FIG. 3, flexible (having flexibility) cables 220 and cables 320 are electrically connected to terminals (not illustrated) disposed in the terminal region 34 of the base material 14 of the radiation detector 10. In the present exemplary embodiment, connection related to a component referred to as a "cable" including the cables 220 and the cables 320 means an electrical connection unless otherwise specified. The cables 220 and the cables 320 include signal lines (not illustrated) consisting of conductors and are electrically connected by connecting the signal lines to the terminals. The cables 220 of the present exemplary embodiment are one example of a first cable according to the embodiment of the present disclosure, and the cables 320 of the present exemplary embodiment are one example of a second cable according to the embodiment of the present disclosure. Hereinafter, in a case where the "cable" is referred to, the cable is flexible (having flexibility).

FIG. 3 illustrates a plan view in which one example of a state where the cables 220 and the cables 320 are connected to the terminal region 34 of the radiation detector 10 of the present exemplary embodiment is seen from the first surface 14A side of the base material 14. As illustrated in FIG. 3, in the present exemplary embodiment, the terminal region 34 is disposed in each of an outer edge portion 14L1 and an outer edge portion 14L2 of the radiation detector 10 having a rectangular shape. A side corresponding to the outer edge portion 14L1 and a side corresponding to the outer edge portion 14L2 are two sides adjacent to each other in the radiation detector 10. In other words, the side corresponding to the outer edge portion 14L1 and the side corresponding to the outer edge portion 14L2 in the radiation detector 10 intersect. The side corresponding to the outer edge portion 14L1 of the present exemplary embodiment is one example of a predetermined side according to the embodiment of the present disclosure, and the side corresponding to the outer edge portion 14L2 of the present exemplary embodiment is one example of a side different from the predetermined side according to the embodiment of the present disclosure.

In the outer edge portion 14L1, one end of a plurality (in FIG. 3, four) of cables 220 is connected to the terminals (not illustrated) of the terminal region 34 by thermocompression. The cables 220 have a function of connecting the driving unit 102 to the scanning wire 26 (refer to FIG. 1). A plurality of signal lines (not illustrated) included in the cables 220 are connected to the scanning wire 26 (refer to FIG. 1) of the sensor substrate 12 through the terminals of the terminal region 34.

The other end of the cables 220 is connected to terminals (not illustrated) disposed in a terminal region 204 of an outer edge portion 202L1 of a driving substrate 202 by thermocompression. A plurality of signal lines (not illustrated) included in the cables 220 are connected to driving components 250 that are circuits, elements, and the like mounted in the driving substrate 202 through the terminals of the terminal region 204.

In FIG. 3, for example, a state where nine driving components 250 (250A to 250I) are mounted in the driving substrate 202 is illustrated. As illustrated in FIG. 3, the driving components 250 of the present exemplary embodiment are arranged in an intersection direction X that is a direction intersecting with a bending direction Y which is a direction along the side corresponding to the outer edge portion 14L1 of the sensor substrate 12.

The driving substrate 202 of the present exemplary embodiment is a flexible printed circuit board (PCB) substrate and is a so-called flexible substrate. The driving substrate 202 of the present exemplary embodiment is one example of a first circuit substrate according to the present disclosure, and the driving components 250 mounted in the driving substrate 202 of the present exemplary embodiment are one example of a first component according to the embodiment of the present disclosure.

The driving components 250 mounted in the driving substrate 202 are components (hereinafter, referred to as the "digital-based components") mainly used for processing a digital signal. A digital buffer, a bypass capacitor, a pull-up/pull-down resistor, a damping resistor, a chip component for electro magnetic compatibility (EMC), and the like are exemplified as a specific example of the driving components 250.

The digital-based components tend to have a relatively smaller area (size) than analog-based components described later. In addition, the digital-based components tend to be more unlikely to be significantly affected by electrical interference, in other words, noise, than the analog-based components are. Thus, in the present exemplary embodiment, a substrate on a side that is bent in accordance with bending of the sensor substrate 12 in a case where the sensor substrate 12 is bent is set as the driving substrate 202 in which the driving components 250 are mounted.

Driving circuit units 212 are mounted in the cables 220. The driving circuit units 212 are connected to the plurality of signal lines (not illustrated) included in the cables 220.

In the present exemplary embodiment, the driving unit 102 is implemented by the driving components 250 mounted in the driving substrate 202 and the driving circuit units 212. The driving circuit unit 212 is an integrated circuit (IC) that includes a circuit different from the driving components 250 mounted in the driving substrate 202 among various circuits and elements implementing the driving unit 102.

The driving unit 102 and the scanning wire 26 are connected to each other by electrically connecting the sensor substrate 12 to the driving substrate 202 through the cables 220.

In the outer edge portion 14L2, one end of a plurality (in FIG. 3, four) of cables 320 is connected to the terminals (not illustrated) of the terminal region 34 by thermocompression. A plurality of signal lines (not illustrated) included in the cables 320 are connected to the signal wire 24 (refer to FIG. 1) through the terminals of the terminal region 34. The cables 320 have a function of connecting the signal processing unit 104 to the signal wire 24 (refer to FIG. 1).

The other end of the cables 320 is electrically connected to connectors 330 disposed in an outer edge portion 304L2 of a signal processing substrate 304. The plurality of signal lines (not illustrated) included in the cables 320 are connected to signal processing components 350 that are circuits, elements, and the like mounted in the signal processing substrate 304 through the connectors 330. For example, connectors having a zero insertion force (ZIF) structure or connectors having a non-ZIF structure are exemplified as the connectors 330. In FIG. 3, for example, a state where nine signal processing components 350 (350A to 350I) are mounted in the signal processing substrate 304 is illustrated. As illustrated in FIG. 3, the signal processing components 350 of the present exemplary embodiment are arranged in the intersection direction X that is a direction along the outer edge portion 14L2 of the base material 14.

The signal processing substrate 304 of the present exemplary embodiment is a non-flexible PCB substrate and is a so-called rigid substrate. Thus, the thickness of the signal processing substrate 304 is greater than the thickness of the driving substrate 202. In addition, the stiffness of the signal processing substrate 304 is higher than the stiffness of the driving substrate 202. The signal processing substrate 304 of the present exemplary embodiment is one example of a second circuit substrate according to the embodiment of the present disclosure, and the signal processing component 350 of the present exemplary embodiment is one example of a second component according to the embodiment of the present disclosure.

The signal processing components 350 mounted in the signal processing substrate 304 are components (hereinafter, referred to as the "analog-based components") mainly used for processing an analog signal. An operational amplifier, an analog-digital converter (ADC), a digital-analog converter (DAC), a power supply IC, and the like are exemplified as a specific example of the signal processing components 350. The signal processing components 350 of the present exemplary embodiment also include a coil around a power supply and a high-capacity smoothing capacitor having a relatively large component size.

As described above, the analog-based components tend to have a larger area (size) than the digital-based components. In addition, the analog-based components tend to be more likely to be affected by electrical interference, in other words, noise, than the digital-based components are. Thus, in the present exemplary embodiment, a substrate on a side that is not bent (not affected by bending) even in a case where the sensor substrate 12 is bent is set as the signal processing substrate 304 in which the signal processing components 350 are mounted.

Signal processing circuit units 314 are mounted in the cables 320. The signal processing circuit units 314 are connected to the plurality of signal lines (not illustrated) included in the cables 320.

In the present exemplary embodiment, the signal processing unit 104 is implemented by the signal processing components 350 mounted in the signal processing substrate 304 and the signal processing circuit units 314. The signal processing circuit units 314 are ICs that include circuits different from the signal processing components 350 mounted in the signal processing substrate 304 among various circuits and elements implementing the signal processing unit 104.

The signal processing unit 104 and the signal wire 24 are connected to each other by electrically connecting the sensor substrate 12 to the signal processing substrate 304 through the cables 320 and the connectors 330.

A method of manufacturing the radiation image capturing apparatus 1 illustrated in FIG. 1 and FIG. 3 will be described with reference to FIG. 4 and FIG. 5.

Figure 4:
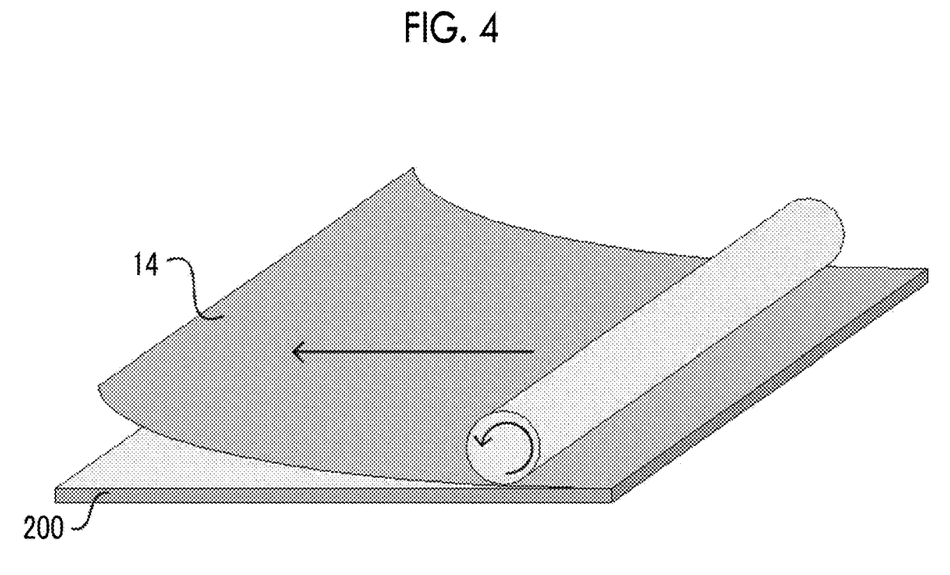
FIG. 4 is a descriptive diagram for describing one example of a method of manufacturing the radiation image capturing apparatus of the first exemplary embodiment.

First, as illustrated in FIG. 4, the base material 14 is formed in a support 200 such as a glass substrate having a greater thickness than the base material 14 through a stripping layer (not illustrated). In the case of forming the base material 14 using a lamination method, a sheet set as the base material 14 is bonded onto the support 200. The second surface 14B of the base material 14 is in contact with the stripping layer (not illustrated).

Furthermore, the pixels 16 are formed on the first surface 14A of the base material 14. In the present exemplary embodiment, for example, the pixels 16 are formed on the first surface 14A of the base material 14 through an undercoat (not illustrated) using SiN or the like.

Furthermore, the conversion layer 30 is formed on the pixels 16. In the present exemplary embodiment, the conversion layer 30 of CsI is directly formed on the sensor substrate 12 as columnar crystal using a vapor deposition method such as a vacuum evaporation method, a sputtering method, and a chemical vapor deposition (CVD) method. In this case, the side of the conversion layer 30 that is in contact with the pixels 16 is set as a base point side of the growth direction of the columnar crystal.

In a case where the conversion layer 30 of CsI is directly disposed on the sensor substrate 12 using the vapor deposition method, for example, a reflection layer (not illustrated) having a function of reflecting the light converted by the conversion layer 30 may be disposed on the surface of the conversion layer 30 on a side opposite to the side in contact with the sensor substrate 12. The reflection layer may directly disposed in the conversion layer 30 or may be disposed through a firm sticking layer or the like. It is preferable to use an organic-based material as the material of the reflection layer. For example, it is preferable to use at least one of white PET, $TiO_2$, $Al_2O_3$, foamed white PET, a polyester-based high reflection sheet, or specular reflection aluminum as the material. Particularly, it is preferable to use white PET as the material from the viewpoint of reflectance. The polyester-based high reflection sheet is a sheet (film) having a multilayer structure in which a plurality of thin polyester sheets are stacked.

In the case of using the scintillator of CsI as the conversion layer 30, the conversion layer 30 can be formed in the sensor substrate 12 using a different method from the present exemplary embodiment. For example, the conversion layer 30 may be formed in the sensor substrate 12 by preparing an aluminum plate or the like on which CsI is vapor-deposited using the vapor deposition method and bonding the side of CsI not in contact with the aluminum plate to the pixels 16 of the sensor substrate 12 using an adhesive sheet or the like. In this case, it is preferable that the entire conversion layer 30 including the aluminum plate in a state of being covered with a protective film is bonded to the pixels 16 of the sensor substrate 12. In this case, the side of the conversion layer 30 that is in contact with the pixels 16 is set as a distal end side of the growth direction of the columnar crystal.

In addition, unlike the radiation detector 10 of the present exemplary embodiment, $Gd_2O_2S$:Tb (GOS) or the like may be used as the conversion layer 30 instead of CsI. In this case, for example, the conversion layer 30 can be formed in the sensor substrate 12 by preparing bonding of a sheet obtained by dispersing GOS in a binder of resin or the like to a support formed by white PET or the like using an adhesive layer or the like, and bonding a side of the GOS to which the support is not bonded to the pixels 16 of the sensor substrate 12 using an adhesive sheet or the like. The case of using CsI in the conversion layer 30 has higher efficiency of conversion from the radiation to the visible light than the case of using GOS.

Furthermore, the plurality of signal lines (not illustrated) included in the cables 220 are electrically connected to the scanning wire 26 (refer to FIG. 1) of the sensor substrate 12 by connecting the cables 220 to the terminals (not illustrated) of the terminal region 34 (refer to FIGS. 2 and 3) of the sensor substrate 12 by thermocompression. In addition, the plurality of signal lines (not illustrated) included in the cables 320 are electrically connected to the signal wire 24 (refer to FIG. 1) of the sensor substrate 12 by connecting the terminals (not illustrated) of the terminal region 34 (refer to FIGS. 2 and 3) of the sensor substrate 12 to the cables 320 by thermocompression.

Furthermore, the plurality of signal lines (not illustrated) included in the cables 220 are electrically connected to the driving components 250 mounted in the driving substrate 202 by connecting the cables 220 to the terminals (not illustrated) of the terminal region 204 (refer to FIG. 3) of the driving substrate 202 by thermocompression.

Figure 5:
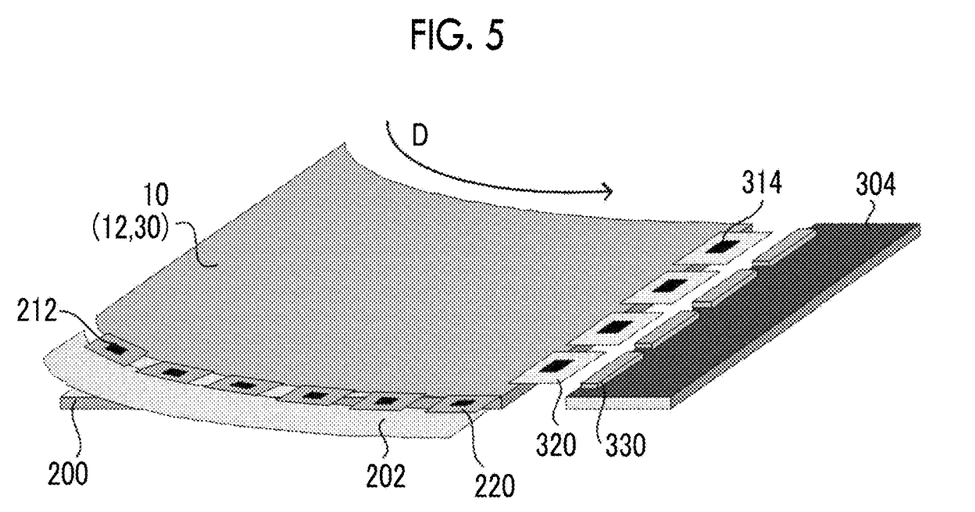
FIG. 5 is a descriptive diagram for describing one example of the method of manufacturing the radiation image capturing apparatus of the first exemplary embodiment.

Then, the radiation detector 10 is stripped from the support 200 as illustrated in FIG. 5. In the case of performing stripping by mechanical stripping, in one example illustrated in FIG. 5, the radiation image capturing apparatus 1 is obtained by performing mechanical stripping by setting the side facing the side to which the cables 320 are connected in the sensor substrate 12 as the starting point of stripping and gradually peeling the sensor substrate 12 from the support 200 in a direction of arrow D illustrated in FIG. 5 from the side set as the starting point to the side to which the cables 320 are connected.

It is preferable that the side set as the starting point of stripping is a side intersecting with the longest side in a case where the sensor substrate 12 is seen in a plan view. In other words, it is preferable that a side in the bending direction Y in which bending occurs due to stripping is the longest side. In the present exemplary embodiment, a side (side corresponding to the outer edge portion 14L1) on the driving substrate 202 side is longer than a side (side corresponding to the outer edge portion 14L2) on the signal processing substrate 304 side. Thus, as described above, the starting point of stripping is set as the side facing the side to which the cables 320 are connected.

In the present exemplary embodiment, furthermore, after the sensor substrate 12 is stripped from the support 200, the cables 320 of the radiation detector 10 are electrically connected to the connectors 330 of the signal processing substrate 304.

The present disclosure is not limited to the present exemplary embodiment. The mechanical stripping may be performed after the cables 320 of the radiation detector 10 are electrically connected to the connectors 330 of the signal processing substrate 304.

In the radiation image capturing apparatus 1 of the present exemplary embodiment, the driving substrate 202 is the flexible substrate as illustrated in FIG. 3 and FIG. 5. Thus, in performing mechanical stripping, the driving substrate 202 is also bent in accordance with bending of the sensor substrate 12.

Unlike the present exemplary embodiment, in a case where a substrate connected to the side of the sensor substrate 12 which corresponds to the outer edge portion 14L1 and is a side in the bending direction Y is not the driving substrate 202, in other words, in a case where the substrate is the signal processing substrate 304, the signal processing components 350 which are analog-based components are bent in accordance with bending of the signal processing substrate 304. In this case, it is likely that the signal processing components 350 mounted in the signal processing substrate 304 are easily damaged or solder for fixing the signal processing components 350 is stripped.

As described above, the analog-based components tend to be more likely to be affected by electrical interference, in other words, noise, than the digital-based components are, and are likely to be affected by damage and the like. Thus, there is a concern that the characteristics of the radiation image capturing apparatus 1 are degraded such that bending of the signal processing substrate 304 accompanied by bending of the sensor substrate 12 affects the signal processing components 350 which are analog-based components, or the image quality of the radiation image is decreased.

Meanwhile, in the radiation image capturing apparatus 1 of the present exemplary embodiment, as described above, the driving components 250 which are digital-based components are mounted in the driving substrate 202 connected to the side which corresponds to the outer edge portion 14L1 and is a side in the bending direction Y. As described above, the digital-based components tend to be more unlikely to be affected by electrical interference, in other words, noise, than the analog-based components are, and are unlikely to be affected by damage and the like. Thus, it is unlikely that the characteristics of the radiation image capturing apparatus 1 are degraded such that bending of the driving substrate 202 accompanied by bending of the sensor substrate 12 affects the driving components 250 which are digital-based components, or the image quality of the radiation image is decreased.

In the present exemplary embodiment, the sensor substrate 12 and the signal processing substrate 304 are connected after the sensor substrate 12 is stripped. Thus, the signal processing components 350 mounted in the signal processing substrate 304 are not affected by bending of the sensor substrate 12.

Second Exemplary Embodiment

Figure 6:
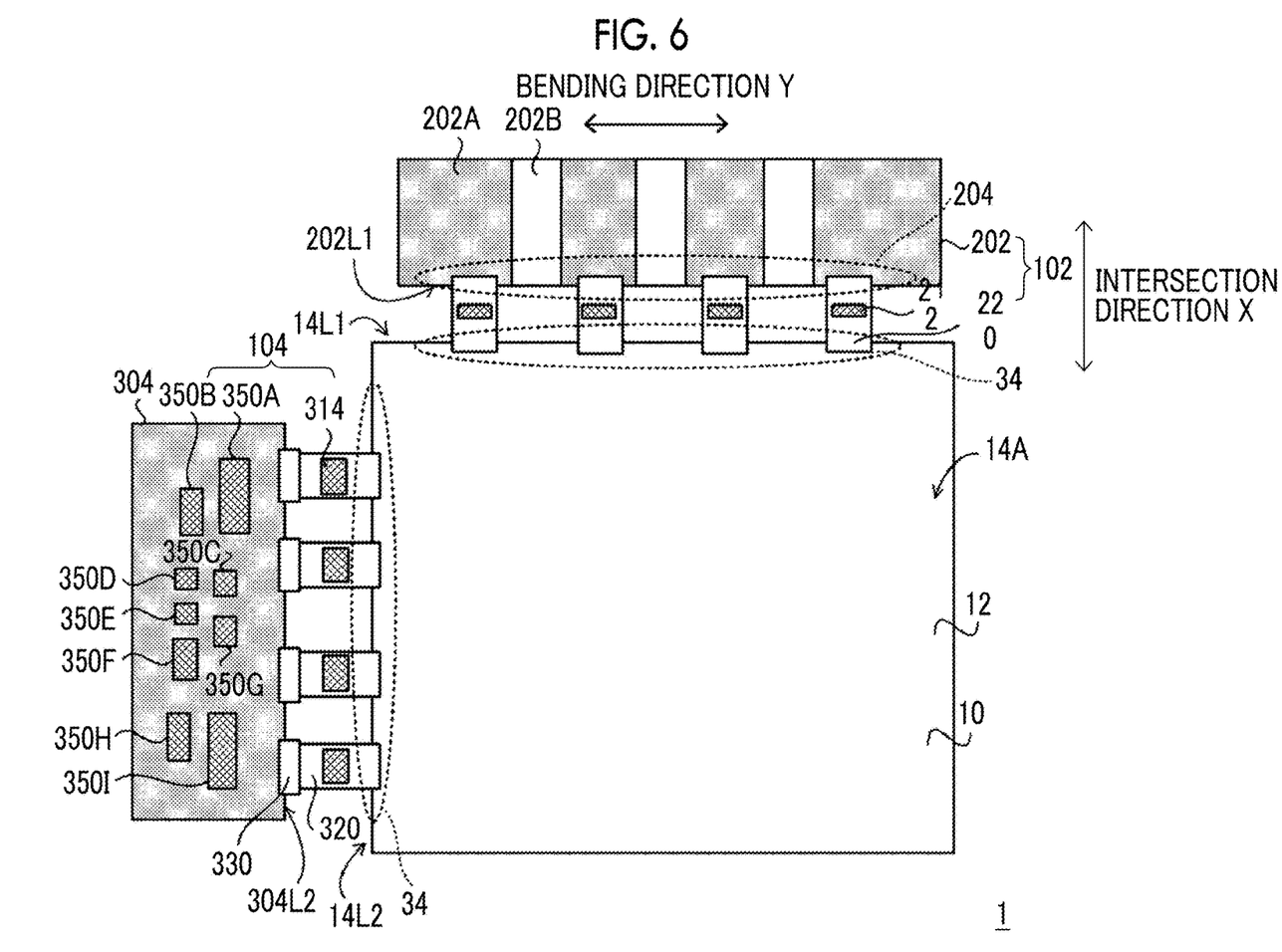
FIG. 6 is a plan view of one example of a radiation image capturing apparatus of a second exemplary embodiment seen from a side of a first surface of a base material.
Figure 7:
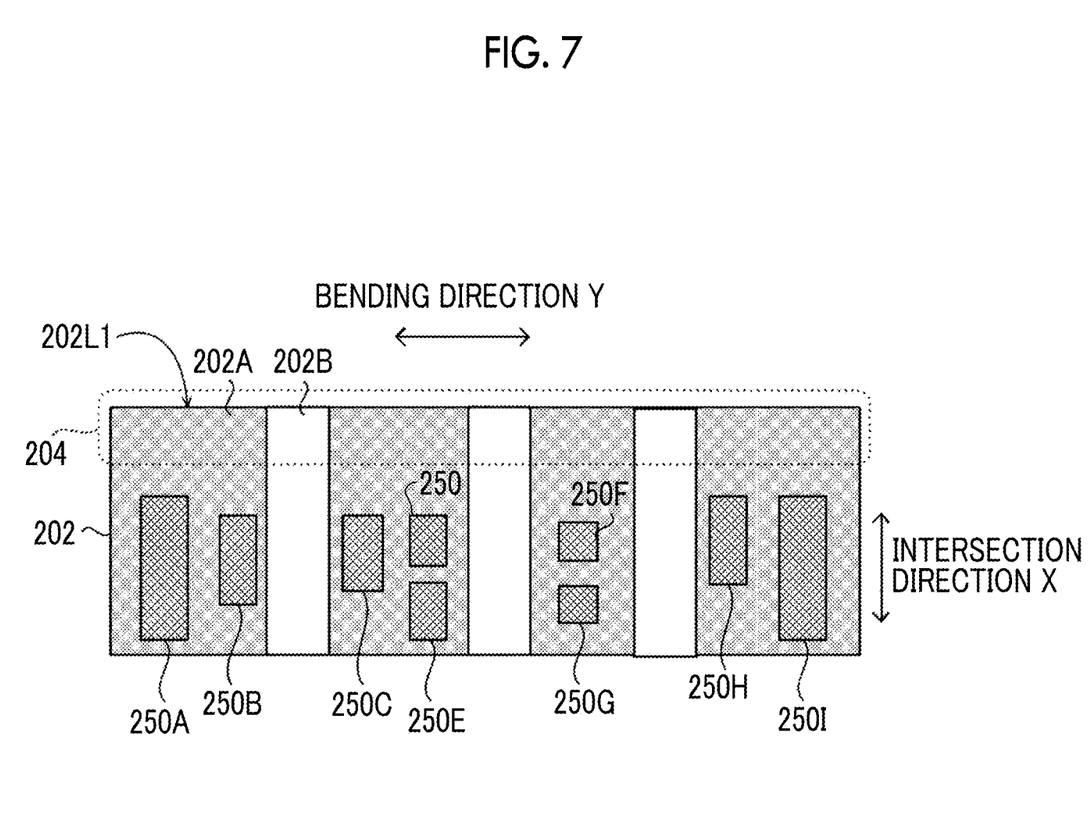
FIG. 7 is a descriptive diagram for describing a state where a driving component is mounted in a driving substrate of the second exemplary embodiment.

FIG. 6 illustrates a plan view in which one example of the radiation image capturing apparatus 1 of the present exemplary embodiment is seen from the first surface 14A side of the base material 14. FIG. 7 illustrates a plan view of one example of the driving substrate 202.

As illustrated in FIG. 6 and FIG. 7, in the radiation image capturing apparatus 1 of the present exemplary embodiment, the driving substrate 202 is different from the driving substrate 202 (refer to FIG. 3) of the radiation image capturing apparatus 1 of the first exemplary embodiment.

As illustrated in FIG. 6 and FIG. 7, the driving substrate 202 of the present exemplary embodiment includes non-flexible regions 202A and flexible regions 202B lined up in the bending direction Y.

The non-flexible regions 202A are so-called rigid substrates like the signal processing substrate 304. Meanwhile, the flexible regions 202B are so-called flexible substrates like the driving substrate 202 of the first exemplary embodiment. A so-called rigid-flexible substrate can be applied as a substrate having the non-flexible regions 202A and the flexible regions 202B.

It is preferable that the driving components 250 are mounted in the non-flexible regions 202A as in one example illustrated in FIG. 7. In addition, it is preferable that the driving components 250 are not mounted along boundaries between the non-flexible regions 202A and the flexible regions 202B.

In the radiation image capturing apparatus 1 of the present exemplary embodiment, even in a case where a part of the driving substrate 202 has the non-flexible regions 202A, the driving substrate 202 is easily bent due to the flexible regions 202B in a case where the radiation detector 10 is bent as in the case of mechanical stripping of the radiation detector 10 from the support 200. Meanwhile, the part of the non-flexible regions 202A is not easily bent. Thus, in the case of bending the driving substrate 202, an effect exerted on the driving components 250 mounted in the non-flexible regions 202A can be further suppressed.

In addition, the thickness of the non-flexible regions 202A is generally greater than the thickness of the flexible regions 202B. By mounting the driving components 250 in a thick region, signal lines, components, or the like can be arranged to be spaced from each other in a thickness direction of the region (flexible regions 202B). Thus, electrical interference such as interference in the driving components 250 from a power supply line can be suppressed. In the present exemplary embodiment, the "power supply line" is a signal line used for supplying a power supply voltage and includes a signal line supplying a ground potential.

In the driving substrate 202, the size and the number of each of the non-flexible regions 202A and the flexible regions 202B are not particularly limited. The arrangement, size, number, and the like of the driving components 250 mounted in the driving substrate 202 may be set in accordance with a manner of bending the sensor substrate 12 (the amount of bending and a radius of curvature R).

As described above, the radiation image capturing apparatus 1 of each exemplary embodiment comprises the sensor substrate 12 including the flexible base material 14 and the plurality of pixels 16 accumulating electric charges generated in accordance with the radiation, the flexible cables 220 of which one end is electrically connected to the terminal region 34 disposed on the side corresponding to the outer edge portion 14L1 of the sensor substrate 12, the driving substrate 202 that is electrically connected to the other end of the cables 220 and in which the driving components 250 of the driving unit 102 used for processing the digital signal in the circuit unit driven in the case of reading out the electric charges accumulated in the plurality of pixels 16 is mounted, the flexible cables 320 of which one end is electrically connected to the terminal region 34 disposed on the side corresponding to the outer edge portion 14L2 of the sensor substrate 12, and the signal processing substrate 304 that is electrically connected to the other end of the cables 320 and in which the signal processing components 350 of the signal processing unit 104 used for processing the analog signal in the circuit unit is mounted.

In the radiation image capturing apparatus 1 of each exemplary embodiment, the driving components 250 of the driving unit 102 used for processing the digital signal are mounted in the driving substrate 202 which is connected to the terminal region 34 disposed on the side corresponding to the outer edge portion 14L1 through the cables 220. In addition, in the radiation image capturing apparatus 1 of each exemplary embodiment, the signal processing components 350 of the signal processing unit 104 used for processing the analog signal are mounted in the signal processing substrate 304 which is connected to the terminal region 34 disposed on the side corresponding to the outer edge portion 14L2 through the cables 320. Accordingly, the effect in a case where the sensor substrate 12 is bent can be suppressed compared to a case where the driving components 250 used for processing the digital signal and the signal processing components 350 used for processing the analog signal coexist in a single substrate.

Particularly, in the case of applying the lamination method as the method of manufacturing the radiation image capturing apparatus 1, the sensor substrate 12 may be mechanically stripped from the support 200 in a state where the cables 220 and 320 and the driving substrate 202 are connected to the sensor substrate 12. In this case, the driving substrate 202 is bent in accordance with bending of the sensor substrate 12 in the case of stripping the sensor substrate 12 from the support 200. However, the effect exerted on the driving components 250 can be suppressed. In addition, according to the radiation image capturing apparatus 1 of each exemplary embodiment, the sensor substrate 12 is easily bent. Thus, the sensor substrate 12 can be easily stripped from the support 200.

While a form in which only the driving components 250 which are digital-based components are mounted in the driving substrate 202 and only the signal processing components 350 which are analog-based components are mounted in the signal processing substrate 304 is described in each exemplary embodiment, the present disclosure is not limited to this form. For example, the analog-based components may be mounted in the driving substrate 202, provided that at least the number of digital-based components is greater than the number of analog-based components. It is preferable that 75% or more are digital-based components, or it is more preferable that only the digital-based components are mounted as in each exemplary embodiment. In addition, for example, the digital-based components may be mounted in the signal processing substrate 304, provided that at least the number of analog-based components is greater than the number of digital-based components. It is preferable that 75% or more are analog-based components, or it is more preferable that only the analog-based components are mounted as in each exemplary embodiment.

In the radiation image capturing apparatus 1 of each exemplary embodiment, it is preferable that a power supply line (not illustrated) supplying power of the power supply for driving the driving circuit unit 212 is disposed in the driving substrate 202 and the cables 220 since the thickness of the base material 14 is relatively small. In other words, it is preferable that the power supply line (not illustrated) is not disposed in the sensor substrate 12. In addition, it is preferable that a signal line (not illustrated) through which a signal for driving the driving circuit unit 212 flows is disposed in the sensor substrate 12 and the cables 220.

The present disclosure is not limited to the radiation image capturing apparatus 1 of each exemplary embodiment. Which of at least one of the driving substrate 202 or the signal processing substrate 304 is to be set as a substrate having flexibility may be set in accordance with a stripping direction in the mechanical stripping of the above manufacturing step. As described above, the signal processing components 350 which are analog-based components mounted in the signal processing substrate 304 tend to be significantly affected by electrical interference, in other words, noise. Thus, it is preferable that the circuits, the elements, and the like mounted in the signal processing substrate 304 are disposed in an environment where it is unlikely to be affected by noise. As described above, the thickness of the rigid substrate is generally greater than the thickness of the flexible substrate. Thus, in the rigid substrate, compared to the flexible substrate, it is possible to increase the distance between the components and the power supply line or the signal line generating noise or make the noise difficult to interfere by stabilizing potential by increasing the thickness of a power supply layer or a ground layer. Accordingly, as in each exemplary embodiment, it is preferable that the signal processing substrate 304 is the rigid substrate.

The driving components 250 which are digital-based components mounted in the driving substrate 202 tend to be more unlikely to be significantly affected by electrical interference, in other words, noise, than the analog-based components are. Thus, the thickness of the driving substrate 202 can be set to be less than the thickness of the signal processing substrate 304. Accordingly, as in each exemplary embodiment, the driving substrate 202 can be set as the flexible substrate.

In the case of manufacturing the radiation image capturing apparatus 1 using the lamination method, the sensor substrate 12 can be mechanically stripped from the support 200 before the driving substrate 202 and the cables 220 are connected to the sensor substrate 12. In this case, the driving substrate 202 and the cables 220 are connected to the sensor substrate 12 after the sensor substrate 12 is stripped from the driving substrate 202. However, since the sensor substrate 12 has flexibility, it is difficult to connect the driving substrate 202 and the cables 220 to the terminals of the terminal region 34 in the sensor substrate 12 by thermocompression, and a positional shift easily occurs. Accordingly, as in each exemplary embodiment, it is preferable that the sensor substrate 12 is stripped from the support 200 after the driving substrate 202 and the cables 220 are connected to the sensor substrate 12.

In each exemplary embodiment, the cables 320 and the signal processing substrate 304 are electrically connected by connecting the cables 320 to the connectors 330 disposed in the signal processing substrate 304. Alternatively, electrical connection may be made by thermocompression without using the connectors 330. As described above, since the signal processing substrate 304 is the rigid substrate, the signal processing substrate 304 tends to have a greater weight than the flexible substrate and is stretched depending on the weight, and it is likely that the cables 320 cause a positional shift in the case of connecting the cables 320 to the signal processing substrate 304 by thermocompression. Thus, as in the radiation image capturing apparatus 1 of each exemplary embodiment, the case of connecting the signal processing substrate 304 to the cables 320 using the connectors 330 results in easy reworking and thus, is preferred. The "reworking" refers to detaching the components and cables connected to the substrate and newly connecting the components and cables again due to a defect, a positional shift, or the like.

While the form of configuring the signal processing unit 104 with the signal processing circuit units 314 and the signal processing substrate 304 mounted in the cables 320 is described in each exemplary embodiment, the present disclosure is not particularly limited thereto. For example, the signal processing unit 104 may be mounted in the cables 320, and the control substrate 110 may be electrically connected to the cables 320 instead of the signal processing substrate 304.

While the aspect in which the pixels 16 are two-dimensionally arranged in a matrix form as illustrated in FIG. 1 is described in each exemplary embodiment, the present disclosure is not limited thereto. For example, one-dimensional arrangement may be used, or honeycomb arrangement may be used. The shape of the pixels is also not limited and may be a rectangular shape or a polygonal shape such as a hexagonal shape. Furthermore, the shape of the active area 15 is not limited.

The radiation detector 10 (radiation image capturing apparatus 1) of each exemplary embodiment may be applied to a so-called irradiation side sampling (ISS) method of arranging the sensor substrate 12 on a side of the conversion layer 30 on which the radiation is incident, in other words, arranging the sensor substrate 12 on a side irradiated with the radiation in the radiation detector 10. In addition, the radiation detector 10 may be applied to a so-called penetration side sampling (PSS) method of arranging the sensor substrate 12 on a side opposite to the side of the conversion layer 30 on which the radiation is incident, in other words, arranging the sensor substrate 12 on a side opposite to the side irradiated with the radiation in the radiation detector 10.

Besides, the configurations, manufacturing methods, and the like of the radiation image capturing apparatus 1, the radiation detector 10, and the like described in each exemplary embodiment are one example and can be changed depending on situations without departing from the gist of the present disclosure.

The entire disclosure of Japanese Patent Application No. 2018-058966 is incorporated in the present specification by reference.

All documents, patent applications, and technical standards disclosed in the present specification are incorporated in the present specification by reference to the same extent as in a case where each of the documents, patent applications, and technical standards is specifically and individually indicated to be incorporated herein by reference.

What is claimed is:

1. A radiation image capturing apparatus comprising:
a sensor substrate including a flexible base material and a plurality of pixels accumulating electric charges generated in accordance with radiation;
a flexible first cable of which one end is electrically connected to a connection region disposed on a predetermined side of the sensor substrate;
a first circuit substrate that is electrically connected to the other end of the first cable;
a flexible second cable of which one end is electrically connected to a connection region disposed on a side different from the predetermined side of the sensor substrate; and
a second circuit substrate that is electrically connected to the other end of the second cable, wherein
the first circuit substrate is mounted with a plurality of first components used for processing a digital signal in a driving unit driven in a case of reading out the electric charges accumulated in the plurality of pixels, and
the second circuit substrate is mounted with a plurality of second components used for processing an analog signal in a signal processing unit driven in the case of reading out the electric charges accumulated in the plurality of pixels.

2. The radiation image capturing apparatus according to claim 1, wherein
the first component includes driving components of a driving unit that reads out the electric charges from the plurality of pixels.

3. The radiation image capturing apparatus according to claim 2, wherein
the second component includes signal processing components of a signal processing unit into which an electric signal corresponding to the electric charges accumulated in the plurality of pixels is input and that generates and outputs image data corresponding to the input electric signal.

4. The radiation image capturing apparatus according to claim 2, wherein the first circuit substrate is a flexible substrate.

5. The radiation image capturing apparatus according to claim 2, wherein
the second circuit substrate is a non-flexible substrate.

6. The radiation image capturing apparatus according to claim 1, wherein
the second component includes signal processing components of a signal processing unit into which an electric signal corresponding to the electric charges accumulated in the plurality of pixels is input and that generates and outputs image data corresponding to the input electric signal.

7. The radiation image capturing apparatus according to claim 6, wherein the first circuit substrate is a flexible substrate.

8. The radiation image capturing apparatus according to claim 6, wherein
the second circuit substrate is a non-flexible substrate.

9. The radiation image capturing apparatus according to claim 1, wherein the first circuit substrate is a flexible substrate.

10. The radiation image capturing apparatus according to claim 1, wherein the first cable is electrically connected to the sensor substrate by thermocompression.

11. The radiation image capturing apparatus according to claim 1, wherein the first cable is electrically connected to the first circuit substrate by thermocompression.

12. The radiation image capturing apparatus according to claim 1, wherein
the second circuit substrate is a non-flexible substrate.

13. The radiation image capturing apparatus according to claim 1, wherein
the second cable is electrically connected to the sensor substrate by thermocompression.

14. The radiation image capturing apparatus according to claim 1, wherein
the second cable is electrically connected to the second circuit substrate through a connector.

15. The radiation image capturing apparatus according to claim 1, wherein
the predetermined side is a longest side of the sensor substrate.

16. The radiation image capturing apparatus according to claim 1, wherein
the first circuit substrate is mounted with some of the plurality of second components smaller than the plurality of first components in number.

17. The radiation image capturing apparatus according to claim 1, wherein
the second circuit substrate is mounted with some of the plurality of first components smaller than the plurality of second components in number.

* * * * *